US00PP17713P2

(12) United States Plant Patent
Stemkens

(10) Patent No.: US PP17,713 P2
(45) Date of Patent: May 8, 2007

(54) ***VERBENA* PLANT NAMED 'CARPUVI'**

(50) Latin Name: *Verbena×hybrida*
Varietal Denomination: Carpuvi

(75) Inventor: Henricus G. W. Stemkens, Hoorn (NL)

(73) Assignee: Syngenta Seeds B.V., Enkuizen (NL)

( * ) Notice: Subject to any disclaimer, the term of this patent is extended or adjusted under 35 U.S.C. 154(b) by 0 days.

(21) Appl. No.: 11/297,580

(22) Filed: Dec. 8, 2005

(51) Int. Cl.
*A01H 5/00* (2006.01)

(52) U.S. Cl. ..... Plt./308

(58) Field of Classification Search ..... Plt./308
See application file for complete search history.

*Primary Examiner*—Kent Bell
*Assistant Examiner*—Annette H Para
(74) *Attorney, Agent, or Firm*—Bruce Vrana

(57) ABSTRACT

A new and distinct variety of *Verbena* plant, substantially as herein illustrated and described, characterized particularly as to novelty by its blue flowers, very early flowering and a habit that is very compact and later spreading.

1 Drawing Sheet

Latin name of the genus and species of the plant claimed: *Verbena×hybrida.*
Varietal denomination: 'Carpuvi'.

BACKGROUND OF THE NEW PLANT

The present invention comprises a new distinct cultivar of *Verbena,* botanically known as *Verbena×hybrida.*

The new cultivar is propagated from cuttings resulting from the cross of 'Z0924-3' and 'Z0637-2'. 'Z0924-3' is a purple flowering *Verbena.* 'Z0924-3' is not commercially and is not known by any synonyms. 'Z0637-2' is a white flowering *Verbena.* 'Z0637-2' is not commercially available and is not known by any synonyms. Neither 'Z0924-3' nor 'Z0637-2' has been patented.

As a result of this cross the present cultivar was created in 2001 in Enkhuizen, Netherlands and has been repeatedly asexually reproduced by cuttings in Enkhuizen, Netherlands and Sarrians, France over a three year period. The new variety is stable and reproduces true to type in successive generations of asexual reproduction.

This new *Verbena* plant is an annual in most climatical zones in the US, only in zones 9 and 10 it is a perennial plant.

DESCRIPTION OF THE DRAWING

This new *Verbena* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Verbena.* The data which defines these characteristics were collected from asexual reproductions carried out in Enkhuizen, Netherlands. The plant history was taken on 14 weeks old plants blossomed under natural light in a greenhouse and grown in a 10.5 cm container.

Color readings were taken in the greenhouse under ambient light. Color references are primarily to The R.H.S. Colour Chart of the Royal Horticultural Society of London.

TABLE 1

Differences between the new cultivar 'Carpuvi,' its parents and a similar cultivar

| | 'Carpuvi' | 'Z0924-3' | 'Z0637-2' | 'Vilena' |
|---|---|---|---|---|
| Flower size | Medium | Small | Large | Small |
| Flower color | Blue | Purple | White | Purple violet |
| Plant habit | Compact | Compact | Vigorous | Vigorous |

The commercial name of the most resembling variety is 'Babylon carpet blue.' The patented name of this variety is 'Vilena' and its U.S. Plant Pat. No. is 12,279.

The plant:

*Classification.*—Botanical: *Verbena×hybrida.*

*Parentage.*—Female parent: A seedling named 'Z0924-3' is one of our seedlings from our Z-generation of plants. Pollen parent: A seedling named 'Z0637-2' is one of our seedlings from our Z-generation of plants.

*Growth habit.*—Compact, later spreading, decumbent.

*Plant height.*—12–14 cm.

*Spreading area of plant.*—32–40 cm.

*Branching character.*—Freely branching and lateral branching at every node.

*Number of branches per plant.*—21–26.

*Blooming period.*—From March until November.

The stem:

*Diameter.*—2–3 mm.

*Length.*—10–15 cm.

*Shape.*—Tetragonal.

*Anthocyanin pigmentation.*—Absent.

*Color of the stem.*—143C.

*Length of internode.*—20–42 mm.

*Pubescence.*—Slightly pubescent.

*Length lateral branches.*—15–19 cm.

The foliage:

*Phyllotaxis.*—Opposite.
*Shape of blade.*—Ovate.
*Texture.*—Upper side: Smooth. Lower side: Smooth.
*Venation.*—Pinnate.
*Leaf margin.*—Incised.
*Leaf base.*—Obtuse.
*Leaf apex.*—Acute.
*Length.*—18–38 mm.
*Width.*—14–26 mm.
*Depth of incision.*—4–10 mm.
*Number of incisions.*—2–6 per leaf.
*Color.*—Upper side: 137A. Lower side: 137C.
*Pubescence.*—Some pubescence is present.
*Length of petiole.*—2–5 mm.
*Petiole surface structure.*—Slightly pubescent.
*Petiole diameter.*—1 mm.
*Petiole coloration.*—143C.

The bud:

*Peduncle length.*—9–19 mm.
*Peduncle diameter.*—1–2 mm.
*Peduncle color.*—143C.
*Budsize.*—Diameter: 2 mm. Length: 8–10 mm.
*Budshape.*—Elongated and ovate.
*Bud color.*—137C.
*Sepals.*—Color (Upper side): 143C. Color (Lower side): 143C. Form: Upright. Number: 5, fused. Length: 7–9 mm. Width: 2 mm. Shape: Elongated. Apex: Emarginate. Base: Fused. Margin: Entire.

The flower:

*Flower diameter.*—14–18 mm.
*Flower height.*—14–18 mm.
*Flower tube length.*—13–17 mm.
*Flower throat diameter.*—2–3 mm.
*Flower throat color.*—155C.
*Inflorescence.*—Corymb.
*Flower-form.*—Single, salverform; sessile on terminal corymbs.
*Petal colour.*—Upper side: N81A. Lower side: N81C.
*Eye.*—No eye.
*Overlapping of petals.*—Separate.
*No. of petals.*—Gamopetalous, 5 lobed.
*Petal apex.*—Obcordate.
*Petal base.*—Fused.
*Petal margin.*—Entire.
*Petal surface texture.*—Smooth.
*Size of the petal.*—Length: 7–9 mm. Width: 6–8 mm.
*Inflorescence.*—Length: 22–30 mm. Diameter: 35–45 mm.
*Calyx length.*—12–14 mm.
*Calyx diameter.*—3–4 mm.
*Anthocyanin pigmentation of calyx limb.*—Absent.
*Color of the calyx.*—137B.
*No. of flowers per inflorescence.*—35–50.
*Fragrance.*—No fragrance.
*Bloom time of one inflorescence.*—New florets continue to open in one corymb over a period of 14 days.
*Lastingness of one flower.*—2–4 days.

The reproductive organs:

*Androecium.*—Stamens quantity: 4. Anther shape: Ovoid. Anther length: 1 mm. Anther color: 145A. Pollen amount: No pollen.
*Gynoecium.*—Pistils quantity: 1. Pistil length: 2.0–2.4 cm. Stigma shape: Bi-lobed. Stigma color: 144C. Style length: 1.9 cm. Style color: 144C. Ovary color: 144C.

Seeds: No seed set is observed.

Roots:

*Type of roots.*—Fibrous, color 155C. Roots start to grow on every part of the stem that contacts the soil, so not only at the nodes.

Physiological and ecological characteristics: Tolerates temperatures ranging from 4 to 35 degrees Celsius.

What is claimed is:

1. A new and distinct cultivar of *Verbena* plant named 'Carpuvi,' as substantially illustrated and described herein.

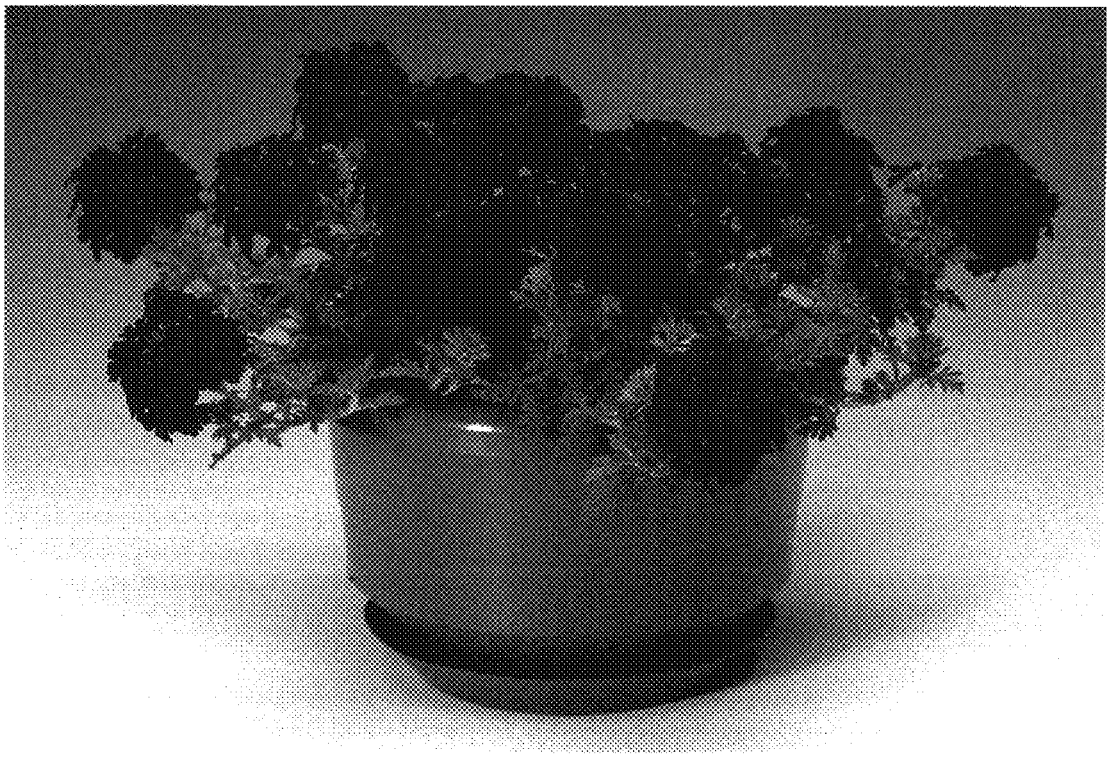

* * * * *